(12) United States Patent
Ingvarsson et al.

(10) Patent No.: US 9,775,662 B2
(45) Date of Patent: Oct. 3, 2017

(54) ELECTRICAL STIMULATION FOR ORTHOPEDIC DEVICES

(71) Applicant: OSSUR HF, Reykjavik (IS)

(72) Inventors: Thorvaldur Ingvarsson, Akureyri (IS); Arni Thor Ingimundarson, Gardabaer (IS)

(73) Assignee: OSSUR HF, Reykjavik (IS)

( * ) Notice: Subject to any disclaimer, the term of this patent is extended or adjusted under 35 U.S.C. 154(b) by 150 days.

(21) Appl. No.: 14/098,657

(22) Filed: Dec. 6, 2013

(65) Prior Publication Data

US 2014/0163444 A1 Jun. 12, 2014

Related U.S. Application Data

(60) Provisional application No. 61/734,222, filed on Dec. 6, 2012.

(51) Int. Cl.
*A61F 5/01* (2006.01)
*A61B 18/00* (2006.01)
(Continued)

(52) U.S. Cl.
CPC ........... *A61B 18/00* (2013.01); *A61F 5/0102* (2013.01); *A61F 5/0123* (2013.01);
(Continued)

(58) Field of Classification Search
CPC ............. A61N 1/36003; A61N 1/0492; A61N 1/0484; A61F 5/0123; A61F 5/0125; A61F 5/0106; A61F 5/0109
See application file for complete search history.

(56) References Cited

U.S. PATENT DOCUMENTS 667,768 A 2/1901 De Puy
1,227,700 A 5/1917 Tucker
(Continued)

FOREIGN PATENT DOCUMENTS

EP 0155815 A2 9/1985
EP 0057561 B1 4/1986
(Continued)

OTHER PUBLICATIONS

Diamond, Laura, et al., "Adduction Moment During Gait in Patients with Moderate & End-Stage Knee Osteoarthritis", ISB XXth Congress—ASB 29th Annual Meeting, Jul. 31-Aug. 5, 2005, Cleveland, Ohio. http://www.asbweb.org/2005-annual-meeting-combined-with-the-isb/.

(Continued)

*Primary Examiner* — Kari Rodriquez
(74) *Attorney, Agent, or Firm* — Workman Nydegger

(57) ABSTRACT

An orthopedic device includes a brace support having at least one strap for providing corrective orientation of a joint and unloading of the joint, and an electrical stimulation system for providing an electrical signal to a user's musculature at or proximate to the joint. The electrical stimulation system provides at least one electrical pulse to the musculature in supplement to the corrective orientation of the joint to induce contraction of the musculature. The electrical stimulation system may include at least one electrode for generating the electrical pulse, and a sensor module for determining movement and orientation of a user's limb for selectively activating the at least one electrode according to predefined criteria and feedback from the sensor module.

6 Claims, 5 Drawing Sheets

(51) Int. Cl.
*A61N 1/36* (2006.01)
*A61N 1/04* (2006.01)
(52) U.S. Cl.
CPC ......... *A61N 1/0484* (2013.01); *A61N 1/0492* (2013.01); *A61N 1/36003* (2013.01)

(56) References Cited

U.S. PATENT DOCUMENTS

| | | |
|---|---|---|
| 1,510,408 A | 9/1924 | Lychou |
| 2,467,907 A | 4/1949 | Peckham |
| 3,046,981 A | 7/1962 | Biggs, Jr. et al. |
| 3,528,412 A | 9/1970 | McDavid |
| 3,548,420 A | 12/1970 | Spence |
| 3,581,741 A | 6/1971 | Rosman et al. |
| 3,751,733 A | 8/1973 | Fletcher et al. |
| 3,820,168 A | 6/1974 | Horvath |
| 3,945,046 A | 3/1976 | Stromgren |
| 3,949,388 A | 4/1976 | Fuller |
| 4,240,414 A | 12/1980 | Theisler |
| 4,246,661 A | 1/1981 | Pinson |
| 4,269,181 A | 5/1981 | Delannoy |
| 4,275,716 A | 6/1981 | Scott, Jr. |
| 4,296,744 A | 10/1981 | Palumbo |
| 4,321,057 A | 3/1982 | Buckles |
| 4,381,768 A | 5/1983 | Erichsen et al. |
| 4,494,950 A | 1/1985 | Fischell |
| 4,506,661 A | 3/1985 | Foster |
| 4,528,440 A | 7/1985 | Ishihara |
| 4,554,913 A | 11/1985 | Womack et al. |
| 4,572,170 A | 2/1986 | Cronk et al. |
| 4,632,098 A | 12/1986 | Grundei et al. |
| 4,655,779 A | 4/1987 | Janowiak |
| 4,685,925 A | 8/1987 | Childress et al. |
| D292,529 S | 10/1987 | Saare |
| 4,712,558 A | 12/1987 | Kidd et al. |
| 4,765,318 A | 8/1988 | Tranberg et al. |
| D298,568 S | 11/1988 | Womack et al. |
| 4,793,333 A | 12/1988 | Marquette |
| 4,796,610 A | 1/1989 | Cromartie |
| 4,805,606 A | 2/1989 | McDavid |
| 4,808,187 A | 2/1989 | Patterson et al. |
| 4,831,531 A | 5/1989 | Adams et al. |
| 4,832,033 A | 5/1989 | Maher et al. |
| 4,854,308 A | 8/1989 | Drillio |
| 4,895,574 A | 1/1990 | Rosenberg |
| 4,923,475 A | 5/1990 | Gosthnian et al. |
| 5,016,621 A | 5/1991 | Bender |
| 5,054,488 A | 10/1991 | Muz |
| 5,085,210 A | 2/1992 | Smith |
| 5,108,456 A | 4/1992 | Coonan |
| 5,133,776 A | 7/1992 | Crowder |
| 5,222,506 A | 6/1993 | Patrick et al. |
| 5,246,463 A | 9/1993 | Giampapa |
| 5,247,938 A | 9/1993 | Silverstein et al. |
| 5,247,945 A | 9/1993 | Heinze et al. |
| 5,253,656 A | 10/1993 | Rincoe et al. |
| 5,258,037 A | 11/1993 | Caspers |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,314,495 A | 5/1994 | Kovacs |
| 5,323,650 A | 6/1994 | Fullen et al. |
| 5,336,269 A | 8/1994 | Smits |
| 5,344,135 A | 9/1994 | Isobe et al. |
| 5,383,845 A | 1/1995 | Nebolon |
| 5,405,405 A | 4/1995 | Love |
| 5,408,873 A | 4/1995 | Schmidt et al. |
| 5,413,611 A | 5/1995 | Haslam et al. |
| 5,415,625 A | 5/1995 | Cassford et al. |
| 5,431,623 A | 7/1995 | Rice |
| 5,432,703 A | 7/1995 | Clynch et al. |
| 5,443,525 A | 8/1995 | Laghi |
| 5,443,528 A | 8/1995 | Allen |
| 5,445,602 A | 8/1995 | Grim et al. |
| 5,449,002 A | 9/1995 | Goldman |
| 5,449,341 A | 9/1995 | Harris |
| 5,458,565 A | 10/1995 | Tillinghast et al. |
| 5,464,443 A | 11/1995 | Wilson et al. |
| 5,468,236 A | 11/1995 | Everhart et al. |
| 5,474,524 A | 12/1995 | Carey |
| 5,476,441 A * | 12/1995 | Durfee ............... A61N 1/36003 434/112 |
| 5,512,039 A | 4/1996 | White |
| 5,542,911 A | 8/1996 | Cassford et al. |
| 5,554,105 A | 9/1996 | Taylor |
| 5,562,605 A | 10/1996 | Taylor |
| 5,569,883 A | 10/1996 | Walter et al. |
| 5,571,208 A | 11/1996 | Caspers |
| 5,619,186 A | 4/1997 | Schmidt et al. |
| 5,620,483 A | 4/1997 | Minogue |
| 5,695,452 A | 12/1997 | Grim et al. |
| 5,718,925 A | 2/1998 | Kristinsson et al. |
| 5,728,167 A | 3/1998 | Lohmann |
| 5,797,864 A | 8/1998 | Taylor |
| 5,823,981 A | 10/1998 | Grim et al. |
| 5,830,136 A | 11/1998 | Delonzor et al. |
| 5,840,047 A | 11/1998 | Stedham |
| 5,842,982 A | 12/1998 | Mannheimer |
| 5,857,988 A | 1/1999 | Shirley |
| 5,857,989 A | 1/1999 | Smith |
| 5,865,776 A | 2/1999 | Springs |
| 5,873,848 A | 2/1999 | Fulkerson |
| 5,888,213 A | 3/1999 | Sears et al. |
| 5,944,661 A | 8/1999 | Swette et al. |
| 5,955,667 A | 9/1999 | Fyfe |
| 5,971,729 A | 10/1999 | Kristinsson et al. |
| 5,993,400 A | 11/1999 | Rincoe et al. |
| 6,010,474 A | 1/2000 | Wycoki |
| 6,030,418 A | 2/2000 | Biedermann |
| 6,063,048 A | 5/2000 | Bodenschatz et al. |
| 6,109,852 A | 8/2000 | Shahinpoor et al. |
| 6,110,138 A | 8/2000 | Shirley |
| 6,125,291 A | 9/2000 | Miesel et al. |
| 6,134,480 A | 10/2000 | Minogue |
| 6,142,965 A | 11/2000 | Mathewson |
| 6,155,120 A | 12/2000 | Taylor |
| 6,231,616 B1 | 5/2001 | Helmy |
| 6,244,873 B1 | 6/2001 | Hill et al. |
| 6,250,651 B1 | 6/2001 | Reuss et al. |
| 6,267,741 B1 | 7/2001 | Lerman |
| 6,287,253 B1 | 9/2001 | Ortega et al. |
| 6,287,268 B1 | 9/2001 | Gilmour |
| 6,289,558 B1 | 9/2001 | Hammerslag |
| 6,301,964 B1 | 10/2001 | Fyfe et al. |
| 6,344,062 B1 | 2/2002 | Abboudi et al. |
| 6,368,295 B1 | 4/2002 | Lerman |
| 6,379,393 B1 | 4/2002 | Mavroidis et al. |
| 6,461,318 B2 | 10/2002 | Freeman et al. |
| 6,500,210 B1 | 12/2002 | Sabolich et al. |
| 6,513,381 B2 | 2/2003 | Fyfe et al. |
| D472,640 S | 4/2003 | Crowe et al. |
| 6,540,703 B1 | 4/2003 | Lerman |
| 6,540,709 B1 | 4/2003 | Smits |
| 6,554,868 B1 | 4/2003 | Caspers |
| 6,560,471 B1 | 5/2003 | Heller et al. |
| D477,409 S | 7/2003 | Mills et al. |
| 6,585,774 B2 | 7/2003 | Dean, Jr. et al. |
| 6,592,538 B1 | 7/2003 | Hotchkiss et al. |
| 6,592,539 B1 | 7/2003 | Einarsson et al. |
| 6,610,101 B2 | 8/2003 | Herr et al. |
| 6,618,934 B1 | 9/2003 | Feldman et al. |
| 6,660,042 B1 | 12/2003 | Curcie et al. |
| 6,666,894 B2 | 12/2003 | Perkins et al. |
| 6,671,531 B2 | 12/2003 | Al-Ali et al. |
| 6,679,920 B2 | 1/2004 | Biedermann et al. |
| 6,728,577 B2 | 4/2004 | Minogue et al. |
| 6,740,123 B2 | 5/2004 | Davalli et al. |
| 6,760,629 B2 | 7/2004 | Minogue et al. |
| 6,761,742 B2 | 7/2004 | Caspers |
| D500,101 S | 12/2004 | Fitzgerald et al. |
| 6,846,331 B2 | 1/2005 | Senoir |
| 6,885,896 B2 | 4/2005 | Minogue et al. |

(56) References Cited

U.S. PATENT DOCUMENTS

| | | |
|---|---|---|
| 6,891,317 B2 | 5/2005 | Pei et al. |
| 6,898,826 B2 | 5/2005 | Draper et al. |
| 6,922,592 B2 | 7/2005 | Thompson et al. |
| 6,939,275 B2 | 9/2005 | Minogue et al. |
| 6,944,503 B2 | 9/2005 | Crowe et al. |
| 6,952,687 B2 | 10/2005 | Andersen et al. |
| 6,969,941 B1 | 11/2005 | Kapps et al. |
| 7,029,500 B2 | 4/2006 | Martin |
| 7,049,732 B2 | 5/2006 | Pei et al. |
| 7,069,089 B2 | 6/2006 | Minogue et al. |
| 7,147,667 B2 | 12/2006 | Bedard |
| 7,150,762 B2 | 12/2006 | Caspers |
| 7,198,610 B2 * | 4/2007 | Ingimundarson ..... A61F 5/0123 602/16 |
| 7,257,448 B2 | 8/2007 | Crowe et al. |
| 7,377,944 B2 | 5/2008 | Janusson et al. |
| 7,396,337 B2 | 7/2008 | McBean et al. |
| 7,438,843 B2 | 10/2008 | Asgeirsson |
| 7,520,864 B2 | 4/2009 | Yeh et al. |
| RE40,875 E | 8/2009 | Minogue et al. |
| D615,209 S | 5/2010 | Minogue et al. |
| 7,747,327 B2 | 6/2010 | Minogue et al. |
| 7,780,741 B2 | 8/2010 | Janusson et al. |
| 8,500,668 B2 | 8/2013 | Siegler et al. |
| 2001/0020143 A1 | 9/2001 | Stark et al. |
| 2002/0052663 A1 | 5/2002 | Herr et al. |
| 2002/0077574 A1 | 6/2002 | Gildersleeve et al. |
| 2002/0082542 A1 | 6/2002 | Hall |
| 2002/0099450 A1 | 7/2002 | Dean, Jr. et al. |
| 2002/0123673 A1 | 9/2002 | Webb et al. |
| 2002/0156654 A1 | 10/2002 | Roe et al. |
| 2002/0165590 A1 | 11/2002 | Crowe et al. |
| 2002/0183646 A1 | 12/2002 | Stivoric et al. |
| 2003/0032907 A1 | 2/2003 | Prahl |
| 2003/0040663 A1 | 2/2003 | Rule et al. |
| 2003/0078674 A1 | 4/2003 | Phillips |
| 2003/0204156 A1 | 10/2003 | Nelson et al. |
| 2004/0010207 A1 | 1/2004 | Flaherty et al. |
| 2004/0019288 A1 | 1/2004 | Kinast |
| 2004/0054311 A1 | 3/2004 | Sterling |
| 2004/0167638 A1 | 8/2004 | Caspers |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0038367 A1 | 2/2005 | McCormick et al. |
| 2005/0159691 A1 | 7/2005 | Turrini et al. |
| 2006/0047215 A1 | 3/2006 | Newman et al. |
| 2007/0106343 A1 | 5/2007 | Monogue et al. |
| 2007/0293911 A1 | 12/2007 | Crowe et al. |
| 2008/0161883 A1 | 7/2008 | Conor |
| 2009/0105795 A1 | 4/2009 | Minogue et al. |
| 2010/0152810 A1 | 6/2010 | Minogue et al. |
| 2010/0234919 A1 | 9/2010 | Minogue et al. |
| 2010/0262044 A1 | 10/2010 | Siegler et al. |
| 2010/0262052 A1 | 10/2010 | Lunau et al. |
| 2010/0312307 A1 | 12/2010 | Minogue |
| 2011/0015696 A1 | 1/2011 | Kirn |
| 2011/0118853 A1 | 5/2011 | Kirn |
| 2011/0218471 A1 | 9/2011 | Ingimundarson et al. |
| 2011/0295339 A1 | 12/2011 | Carroll |
| 2012/0059298 A1 | 3/2012 | Hoffman et al. |
| 2013/0165830 A1 | 6/2013 | Siegler et al. |

FOREIGN PATENT DOCUMENTS

| | | |
|---|---|---|
| EP | 0201271 B1 | 5/1996 |
| EP | 0938912 A1 | 9/1999 |
| EP | 1144045 B1 | 5/2003 |
| EP | 2198915 A1 | 6/2010 |
| EP | 2260900 A1 | 12/2010 |
| EP | 2263743 A1 | 12/2010 |
| GB | 2092004 A | 8/1982 |
| GB | 2136294 A | 9/1984 |
| GB | 2156682 A | 10/1985 |
| GB | 2175806 A | 12/1986 |
| GB | 2311013 A | 9/1997 |
| GB | 2359758 A | 9/2001 |
| GB | 2369998 A | 6/2002 |
| GB | 2374288 A | 10/2002 |
| GB | 2378903 A | 2/2003 |
| GB | 2395142 A | 5/2004 |
| GB | 2438589 A | 12/2007 |
| GB | 2457025 A | 8/2009 |
| IE | 66405 S | 12/1995 |
| IE | 80999 S | 8/1999 |
| IE | 20000018 A2 | 8/2000 |
| IE | 20010651 A2 | 1/2003 |
| WO | 00/41764 A1 | 7/2000 |
| WO | 02/066111 A1 | 8/2002 |
| WO | 02/068040 A2 | 9/2002 |
| WO | 02/074109 A2 | 9/2002 |
| WO | 03/006106 A2 | 1/2003 |
| WO | 2004/087262 A2 | 10/2004 |
| WO | 2004098703 A2 | 11/2004 |
| WO | 2006/100609 A1 | 9/2006 |
| WO | 2007/138071 A1 | 12/2007 |
| WO | 2008/005865 A1 | 1/2008 |
| WO | 2009/095801 A1 | 8/2009 |
| WO | 2010/067145 A1 | 6/2010 |
| WO | 2010/087899 A2 | 8/2010 |
| WO | 2011/153213 A1 | 12/2011 |
| WO | 2012/047737 A2 | 4/2012 |

OTHER PUBLICATIONS

"Quattromed® brochure", Neurotech® UK/Ireland, Nov. 2012. http://www.neurotechgroup.com/uk/products/quattromed.

"Quattromed® XP, OA Knee Brace brochure" Neurotech® UK/Ireland, Nov. 2012.

International Search Report from PCT Application No. PCT/US2013/073378, Feb. 6, 2014.

* cited by examiner

ELECTRICAL STIMULATION FOR ORTHOPEDIC DEVICES

FIELD OF THE DISCLOSURE

This disclosure relates to orthopedic devices, and more particularly to orthopedic devices providing corrective support and/or joint adjustment in combination with electrical stimulation of surrounding or proximate musculature.

BACKGROUND

Orthopedic devices, such as braces, are periodically rejected due to the tendency of muscles weakening because of wearer over reliance of the brace. This phenomenon occurs when the brace immobilizes the target condition it should treat, such as osteoarthritis, by delaying eventual recovery. The wearer may become more reliant on the brace for support and less reliant on the actual muscles for stabilizing the joint.

In the example, osteoarthritis is a progressive degenerative joint disease that often results in disability and a loss of joint function. Osteoarthritis of the knee may be debilitating since the knee is stressed from daily activities, such as walking up and down stairs, or even when resting. Osteoarthritis causes a gradual breakdown of the cartilage in the joints. As the disease progresses and cartilage wears away, the bones rub and grind against each other cause pain.

Knee osteoarthritis is a chronic degenerative condition in that it gradually worsens. In the early stages of development, people often cut back on their activities or work because of discomfort and pain. Advanced knee osteoarthritis is associated with pain, stiffness and inflammation.

In a healthy knee, cartilage covers the ends of the bones and prevents them from rubbing against each other. As the surface of the cartilage breaks down, small cracks and indentations may form. In a mild case of osteoarthritis, the knee might show signs of varus misalignment. Over time, sections of cartilage wear down, reducing flexibility and increasing the likelihood of becoming damaged by daily activities. The lubricating fluid (synovial fluid) breaks down and become less effective, while cracks and pits continue to appear in cartilage. As the knee degenerates, the leg develops a bowed appearance.

In severe osteoarthritis, bones are left unprotected as large sections of the cartilage are worn away, resulting in pain from bones grating against each other as they move. Pain and damage may arise from small fragments of cartilage that have become detached and may be floating around the joint. Externally, the leg will often appear severely bowed in relation to the thigh.

Many braces used to address osteoarthritis immobilize the knee and take up some muscle function used otherwise by the user's muscles. These braces can often eliminate or postpone the need for surgery, and have none of the effects of pain-relief medication. The braces have a tendency to replace or minimize quadriceps function. Quadriceps weakness, however, is also a cause for development of osteoarthritis of the knee and is one of the issues that a physical therapist attempts to rehabilitate when treating a user with osteoarthritis of the knee. By treating the knee with a brace, improvement of muscle weakness is inhibited and the user is unable fully recover muscle strength.

As well understood, the quadriceps muscles are the muscles in the anterior surface of the thigh, and include four separate muscles groups: rectus femoris, vastus lateralis, vastus medialis, and vastus intermedius. Quadriceps weakness is commonly associated with osteoarthritis of the knee is widely believed to result from disuse atrophy secondary to pain in the involved joint. Quadriceps weakness is a primary risk factor for knee pain, disability, and progression of joint damage in persons with osteoarthritis of the knee.

Studies have shown regular, moderate exercise is also beneficial to arthritis sufferers. It helps keep the joints flexible and increases the range of motion. When one exercises, the body releases endorphins, which are natural painkillers. It is therefore advantageous not only to use and strengthen the muscles, but moderate usage of the muscles can improve the condition of osteoarthritis sufferers.

It has been found that certain orthopedic devices provide dynamic strengthening of muscle groups when stabilizing a joint. A dynamic osteoarthritis knee brace ("OA brace") includes straps arranged to load muscle groups between extension and flexion during gait, as described in U.S. Pat. No. 7,198,610, issued on Apr. 3, 2007 and incorporated by reference. In the OA brace, force straps exert a load on the quadriceps through dynamic extension resistance while unloading compartments of the knee to provide correct joint orientation.

FIGS. 1A and 1B exemplify known OA braces having one or more force straps. In FIG. 1A, the OA brace employs a medial upright with a valgus bend plus an opposing dynamic force strap to generate a three-point leverage system that unloads the medial compartment of the knee. The quadriceps resist the load as the knee goes into extension actively allowing for some quadriceps use to maintain some strength of the leg while wearing a brace.

FIG. 1B shows a similar three-point leverage system by including a flexible upright and including dual dynamic force straps to disperse the counter force that the quadriceps resist across two points of contact. The force on the knee is arranged to reduce the pressure on the affected part of the knee, resulting in reduction in pain, and allowing the patient to use the knee normally and more frequently.

Some users wearing the aforementioned OA braces may not understand when to activate the quadriceps during a gait cycle, particularly at certain points, or they may require additional muscle strengthening at the quadriceps or other areas such as the gluteus medius to assure better corrective therapy for treating osteoarthritis of the knee.

As discussed herein, electrical stimulation may be of the type commonly referred to as Transcutaneous Electrical Nerve Stimulation (TENS) used primarily as a pain blocker by creating a buzzing sensation that blocks a pain signal from the nerve where it is perceived in the brain as pain. Electrical Muscle Stimulation or Neuromuscular Electrical Stimulation (NMES) is used to affect the muscle by targeting it to prevent retardation or muscular disuse atrophy, and provide relaxation of muscle spasms, muscle reeducation, blood circulation and activation. The intensity of either TENS or NMES may be modified accordingly to increase cocontraction.

TENS and NMES are interchangeably referred to herein to as "electrical stimulation," with the recognition that the type of stimulation may vary according to its particular application (i.e., pain blocking or muscle activation, respectively).

NMES is the elicitation of muscle contraction using electric impulses and has received increasing attention in the last few years because it has the potential to serve as: a strength training tool; a rehabilitation and preventive tool for partially or totally immobilized patients; a testing tool for evaluating the neural and/or muscular function in vivo; and a post-exercise recovery tool for individuals. The impulses are generated by a device and delivered through electrodes on the skin in direct proximity to the muscles to be stimulated. The impulses mimic the action potential coming from the central nervous system, causing the muscles to contract.

SUMMARY

An orthopedic device according to the disclosure may be arranged for immobilization or joint correction and has an electrical stimulation system for activating muscle groups and/or providing user feedback on how to activate muscle groups during a gait cycle or other joint movement. The orthopedic device may achieve at least one of the following: (a) reduce pain by disrupting the pain signals, (b) stimulate the muscles such as the vastus medialis, vastus lateralis, and gluteus medius to reduce an additional load onto the affected compartment for better protection of cartilage and reduction in pain, and (c) mildly stimulate muscles to provide user feedback on how to modify a gait pattern to reduce a load on the affected compartment.

A first embodiment of the orthopedic device includes a brace support in combination with a garment, such as a sleeve or brace liner, having an electrical stimulation system including sensors arranged to detect gait position or other joint movement. Electrodes mounted on the garment are adapted to activate muscle groups upon detection of certain criteria requiring activation of muscles in a healthy joint.

In the instance of a gait cycle of a leg, the activation of muscles may occur at certain locations of a normal gait. The muscles are gradually or periodically activated during extension of a leg. The electrical stimulation system may also be adapted to activate muscle groups upon detection of certain conditions such as when a user walks up or down stairs.

According to a method of the disclosure, the orthopedic device is donned with the brace support over the garment carrying the electrical stimulation system. The garment includes a plurality of sensors that continuously sense and analyze motion. A processor may be provided which calculates the movement of the joint and directs an appropriate response by stimulating preselected muscle groups.

Accelerometers and sensors (for displacement, force and angle) may sample joint motion by identifying specific joint motion events such as gait. The motion is analyzed continuously, with gait pattern recognition algorithms detecting when a user is walking on slopes, stairs (up or down), and remaining stationary or seated. If it is determined the user is on an incline the processor sends signals to electrodes mounted at various positions of the garment in communication with the electrical stimulation system for causing activation, such as contraction, of muscles and/or muscle groups at various selected levels. The electrical stimulation may be dynamic in that it varies during gait according to muscle activity at any point.

Alternatively to the electrical stimulation for activating muscle groups, the level of stimulation may be more attenuated to provide biofeedback to the user as a reminder to use muscles, particularly in combination with the support at various positions of the joint.

The apparatus carrying the electrodes may be arranged in a variety of configurations to cover different muscle groups. Regarding a garment provided for a user with osteoarthritis, the sleeve may be adapted to include electrodes at the quadriceps and gluteus medius to provide more complete realignment of the knee through muscle stimulation.

Alternatively or besides the aforementioned sampling of motion, the sensor system may be adapted according to different severities of osteoarthritis. The adduction moment of the knee is considered a factor most correlated with knee osteoarthritis. The sensor system can be adapted to detect gait and activate electrodes at levels under the gait moment adduction during the gait cycle, as the overall magnitude of the adduction waveform over the gait cycle increases with both disease and severity level of osteoarthritis.

The sensor system may have a plurality of different sequences stored according to severities of osteoarthritis derived from adduction moments. The electrodes are activated according to the percent of the gait cycle and the severity of the osteoarthritis, as derived from different and corresponding adduction moments.

Under the described embodiments, the electrical stimulation may be TENS to alleviate pain, or may be NMES to activate muscle groups or to provide minimal sensory feedback.

Besides modifying the electrical stimulation system during a joint movement cycle, the electrical stimulation system can be modified or programmed to provide electrical stimulation at different times of the day. Alternatively, the electrical stimulation system can be activated during physical activity (i.e., on or off), or it can be selectively programmed to provide electrical stimulation upon certain conditions during physical activity (dynamically controlled).

The brace support may have electrodes incorporated therein. Electrodes of the electrical stimulation system may be incorporated into the spacer elements, as taught in U.S. Pat. No. 7,198,610, so electrical stimulation is applied to the user at areas adjacent to the spacer elements. These spacer elements can be selectively on particular areas of a rehabilitative orthopedic device carrying such spacer elements. Further, the layers of the spacer element and the electrodes, irrespective of any supporting device, can be combined in a single unit and applied with suitable strapping or other means for application in providing electrical stimulation.

In continuing referring to U.S. Pat. No. 7,198,610, the various straps can be adapted to incorporate the electrodes of the electrical stimulation system; alternatively additional pads may be added to the straps or at other locations to enable electrode stimulation. The brace of the '610 patent is primarily arranged for treatment of osteoarthritis. Such electrical stimulation system electrodes are advantageous for incorporation into the brace and the straps or spacer elements for additional treatment of arthritis of the knee in combination with the other features of the brace of the '610 patent.

Particularly, the orthopedic device can measure and provide feedback on range of motion (ROM). The electrical stimulation system can be employed throughout the range of motion, and may selectively provide stimulation at certain points through the range of motion. Alternatively, an electrode matrix of the electrical stimulation system may be relied on to provide stimulation at various stages throughout the range of motion depending on when it is determined that additional muscular activity is required. Electrical stimulation may be in combination with the ROM measurement and feedback, and the electrical stimulation system to measure muscular activity throughout the range of motion.

BRIEF DESCRIPTION OF THE DRAWINGS

The inventive orthopedic device is described referring to the accompanying drawings showing preferred embodiments according to the device described. The device as disclosed in the accompanying drawings is illustrated for example only. The elements and combinations of elements described below and illustrated in the drawings can be arranged and organized differently to result in embodiments still within the spirit and scope of the device described.

DETAILED DESCRIPTION OF VARIOUS EMBODIMENTS

A. Overview

Figure 1A:
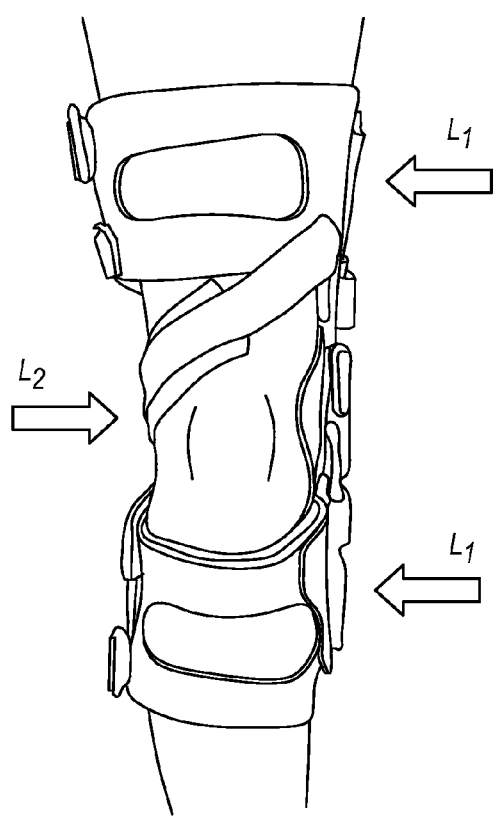
FIGS. 1A and 1B are schematic views showing loads on a leg of a user from an osteoarthritis knee support.
Figure 1B:
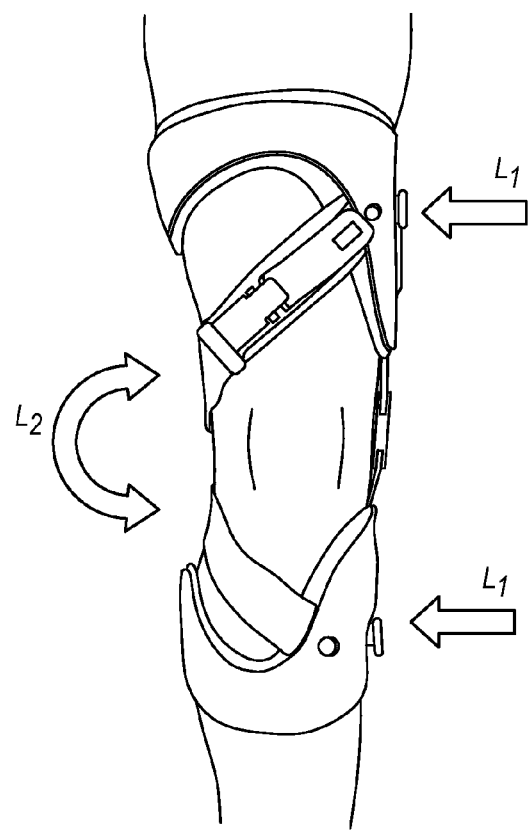

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings. They also will be described below. It should be understood, however, there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

Figure 2:
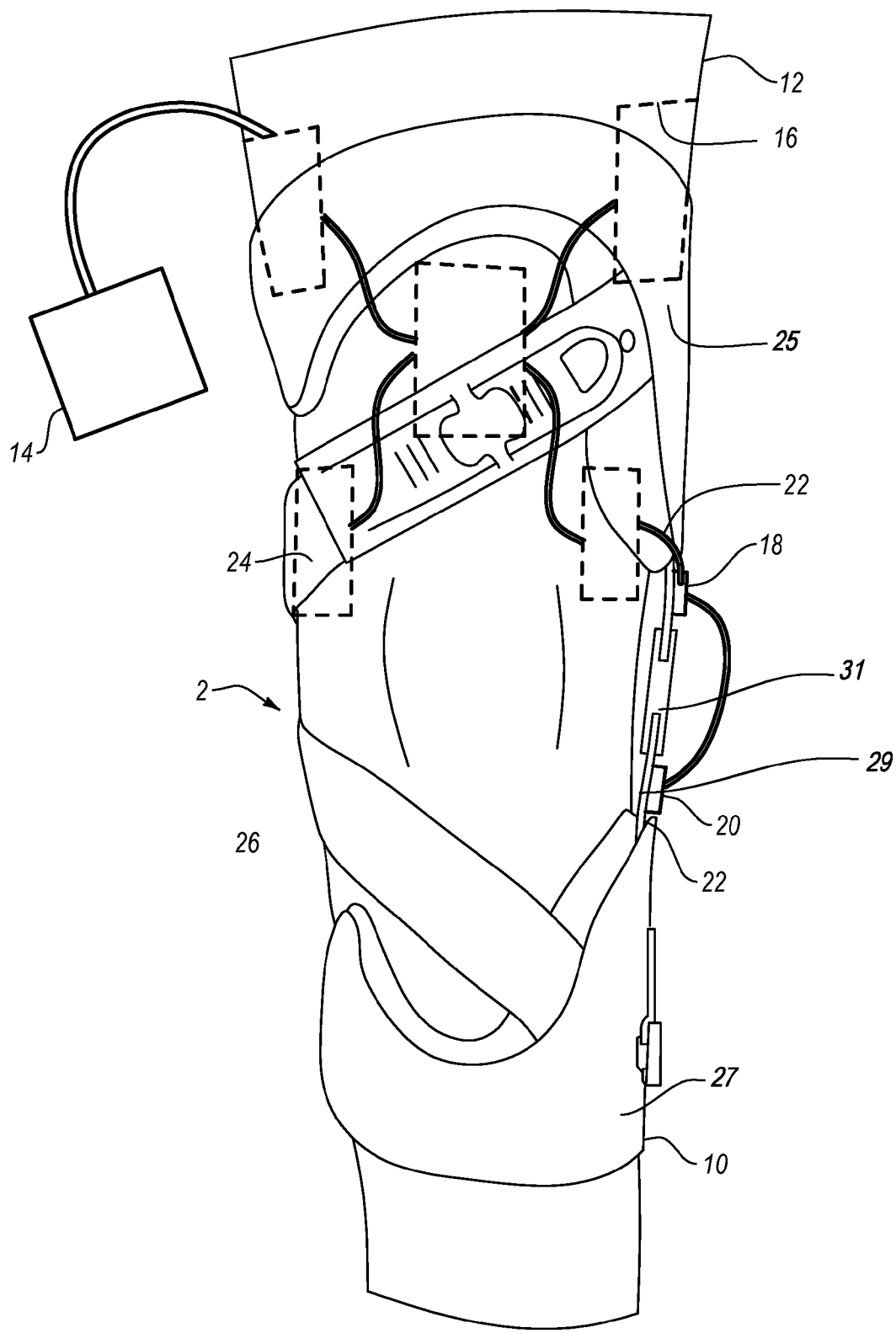
FIG. 2 is a schematic view showing an embodiment of an orthopedic device.

FIG. 2 provides an exemplary embodiment of an orthopedic device 2 having both a knee support 10 and a garment 12. The knee support 10 is in the form of an OA brace generally of the type described in U.S. Pat. No. 7,198,610, whereas the garment 12 is in the form of a sleeve. The garment 12 includes an electrical stimulation system including a controller/processor 14 and a plurality of electrodes 16 connected to the controller 14. At least one sensor or accelerometer 18, 20 is either on the OA brace 12 (such as on the struts 22) or on the garment 12.

As shown in FIG. 2, the first and second straps 24, 26 secure to upper and lower frame portions 25, 27. The upper and lower frame portions 25, 27 are connected to one another by an upright 29 including a hinge 31, as discussed in connection with U.S. Pat. No. 7,198,610. The first and second straps 24, 26 are arranged to urge a dynamic force counteracted by the upright 29 depending upon articulation of the hinge 31.

Support may be of any type of brace, and is not limited to the leg or knee. The garment may be formed from a textile or other suitable material providing a low-profile, lightweight soft device.

The OA brace 10 includes straps 24, 26 applied a load to the knee, which the quadriceps resists at least in part the load on the knee. From this recognition, the user can strengthen or at least use the quadriceps to inhibit the possibility of atrophy. When combined with the garment 12, the electrodes 16 can activate certain muscles, such as the quadriceps, at certain stages of the gait cycle (such as at extension). Alternatively, the electrodes 16 may provide a signal to the user to activate certain muscles on his own to know when to tighten, contract or otherwise employ, his muscles at particular stages of the gait cycle and activate muscles despite wearing a knee support. In yet another alternative, the electrodes can be arranged to block pain at strategic locations about the knee.

When used in supplement to the OA brace, the electrical stimulation system allows for improved activation of certain muscles by electrical stimulation, enhancing the impact from the OA brace. In the instance of an OA brace configured to provide pain relief from compartmental arthritis of the knee, the electrical stimulation system can strengthen the certain muscle groups and cause them to activate in a timely manner.

The electrical stimulation system can be adapted so it is dynamically increased or decreased over the gait cycle or activated from on and off settings at certain positions of the gait cycle. The electrical stimulation system can adapt to various walking conditions, such as inclines and stairs, to provide the stimulation over changed conditions.

The garment 12 may be worn over the leg with or without the OA brace. If the user has reached a certain strength level of the leg and respective muscles and the OA brace is unnecessary, the garment 12 be used alone as a reminder to the user of when to use certain muscles in a gait cycle, or can activate muscles at certain movements.

Figure 3:
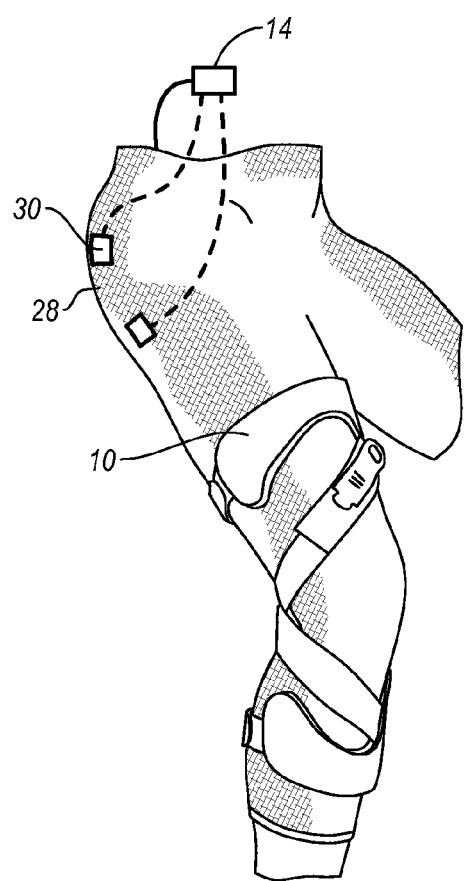
FIG. 3 is a schematic view showing another embodiment of an orthopedic device.

The embodiment of FIG. 3 exemplifies a garment 28 not limited locally to the OA brace 10, but extends to certain muscles including the gluteus medius with electrodes 30. It has been found that knee issues are related to the hip muscles so that working the quadriceps may not be sufficient for some users. Connection of electrodes 30 to the gluteus medius and/or other relevant muscles may attribute to enhanced realignment of the knee in combination with the OA brace.

The electrical stimulation system, at least for treatment of osteoarthritis of the knee, may be arranged according to the adduction moment gait waveform of the user or may be selectable among a variety of osteoarthritis stages. The controller/processor may include a menu by which the user can select different levels of electrical stimulation indexed to various adduction moment gait waveforms. As the user goes through the gait cycle, and the movement of the user is tracked by the electrical stimulation system, the electrical stimulation is activated according to a selected level. The electrical stimulation is dynamic in that it varies according to the gait cycle.

Figure 4:
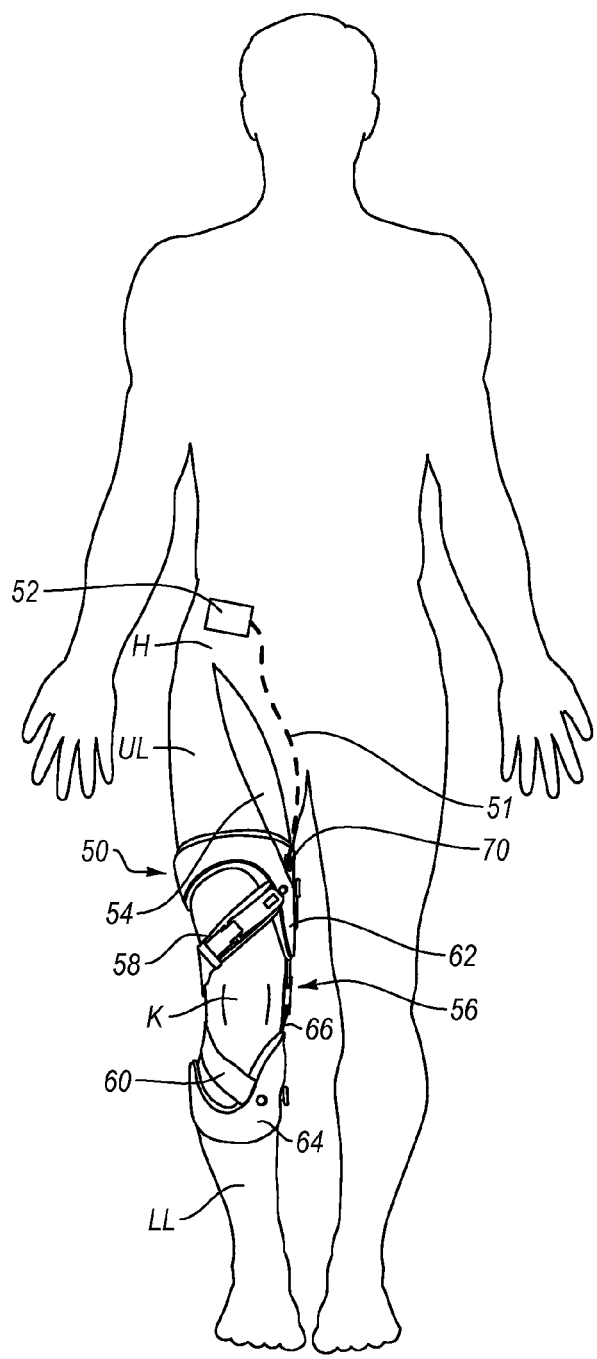
FIG. 4 is a schematic view showing another embodiment of an orthopedic device over the leg of the wearer.
Figure 5:
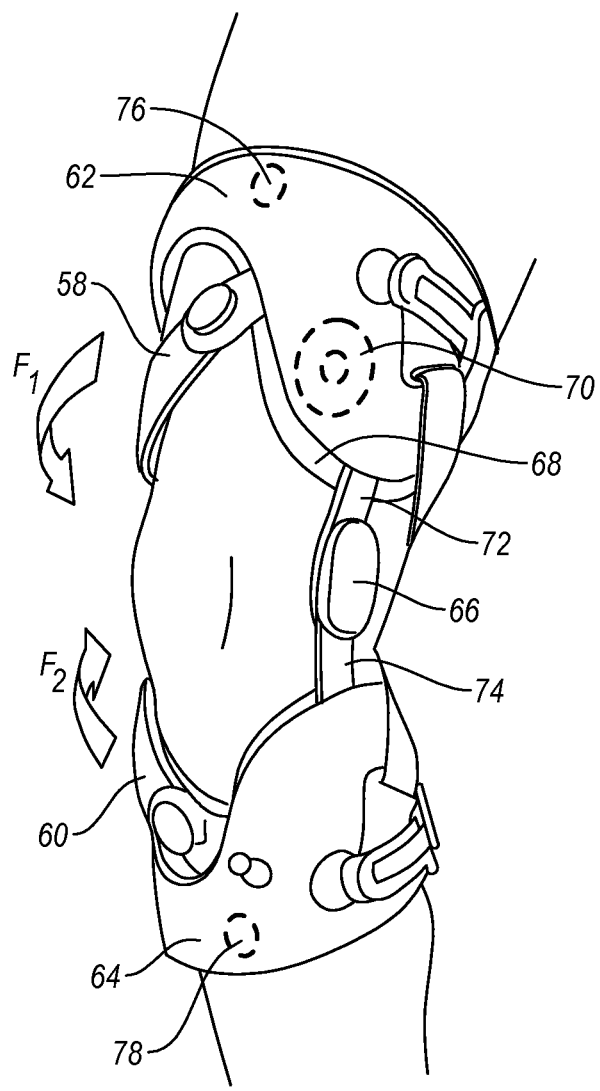
FIG. 5 is a detailed view showing the orthopedic device of FIG. 4.
Figure 6:
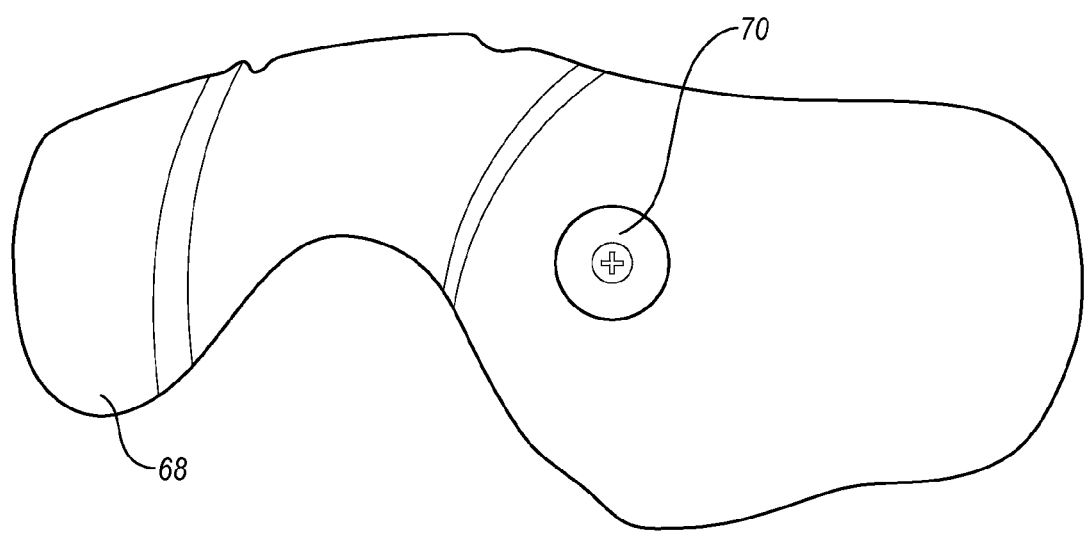
FIG. 6 is a detailed view of a liner used in the orthopedic device of FIG. 5.

In the embodiment of FIGS. 4-6, an orthopedic device 50 includes a brace support 56 having the general configuration of the OA brace 10 having at least one strap 58, 60) for providing corrective orientation of a joint and unloading of the joint. The OA brace 56 includes an upper frame 62 connected to a lower frame 64 mounted on the lower leg portion LL by upper and lower struts 72, 74 secured to one another by a hinge 66.

The orthopedic device 50 has an electrical stimulation system 51 for providing an electrical signal to a user's musculature at or proximate to the joint. The electrical stimulation system 51 provides at least one electrical pulse to the musculature in supplement to the corrective orientation of the joint to induce contraction of the musculature. The electrical stimulation system may include at least one electrode (70) for generating the electrical pulse and a control unit 52 connected at the user's hip H or waist and the at least one electrode 70.

The connection of the control unit 52 may be to a belt or garment that holds the control unit as the user wears the device and undergoes movement. The control unit 52 connects to the least one electrode 70 mounted on a thigh liner 68 carried by an upper frame 62 of the OA brace extending over the upper leg portion UL.

The orthopedic device includes a sensor module for determining movement and orientation of a user's limb for selectively activating the at least one electrode according to predefined criteria and feedback from the sensor module. The sensor module may include sensors 76, 78 at various locations of the brace support 56.

Force straps 58, 60 extend between the upper and lower frames 62, 64, and arranged to spiral about the user's upper and lower leg portions UL, LL. The force straps 58, 60 tighten around the upper and lower leg portion UL, LL and exert forces on the knee F1, F2 when the user's leg goes into extension.

The electrode 70 is aligned or arranged proximate to the vastus medialis 54 of the user's upper leg portion UL. Placing the electrode 70 on the liner 68 assures proper alignment of the electrode 70 with the vastus medialis. The electrode 70 may be secured to the liner by glue or detachably secured by hook and loop fasteners, or by other means. The liner may be of the type described in U.S. patent application publication no. 2011/0218471, published on Sep. 8, 2011 and incorporated in its entirety. Multiple electrodes may be installed on the liner or at other select portions of the OA brace or separate components.

The control unit 52 is arranged to provide a signal to the electrode 70 depending on a variety of factors. The control unit can have both pre-set programs arranged to deliver both TENS and NMES signals depending on the desired treatment.

According to a variation, the control unit has a gait setting arranged to change control to an accelerometer attached to the lower frame of the device 50. The accelerometer can detect changes in gait speed and the type of gait the person of walking. Differences in gait include walking on level ground, up/down stairs or incline, or the speed of the gait such as for walking or running. Depending on the type of gait, the electrode is controlled or modified in intensity and function to provide stimulation to the vastus medialis depending on the load level going through the affected compartment. The function of the electrode may be activated only as needed, just as the force straps of the OA brace only apply force as need.

The control unit may be arranged to allow the user to adjust the level of stimulation applied both during the present conditions and during the gait pattern control. This arrangement considers a predetermined severity of osteoarthritis in correlation to the pain the user experiences prior to getting the orthopedic device. Users having more pain may require a higher level of stimulation during gait than users with less pain.

Figure 7:
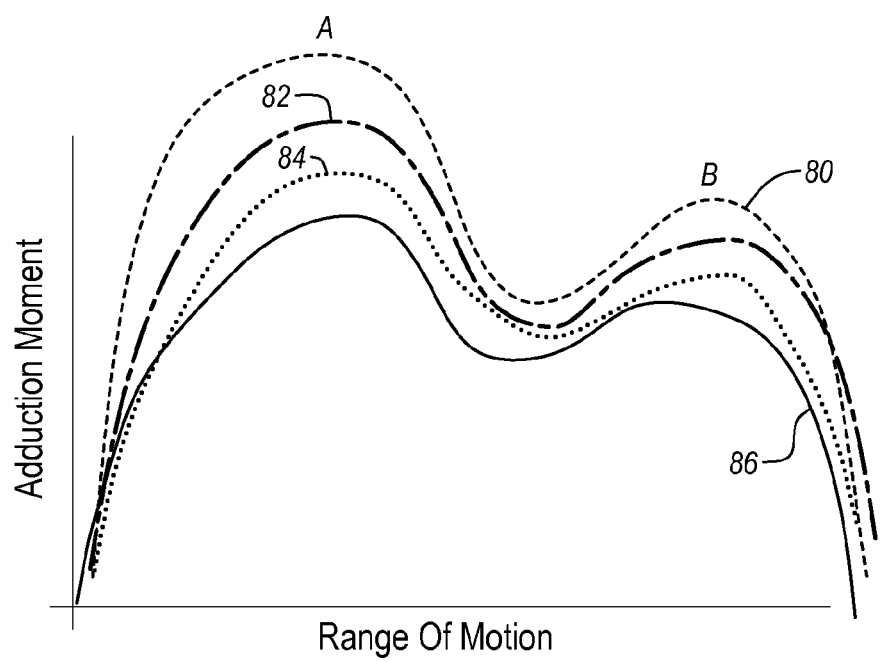
FIG. 7 is an exemplary graph showing the stimulation over positions of gait.

In observing FIG. 7, a graph shows how the orthopedic device affects the user's pain over a gait cycle. The x-axis is the range of motion of the knee showing the complete stance phase, and the y-axis is the adduction moment going through the knee. The peak A represents the highest adduction moment going through the knee right after heel strike at 0 degrees. The peak B is at push off with the knee at full extension.

Reference line 80 illustrates a user having osteoarthritis pain over gait with the peaks representing extension and flexion, and reference line 86 represents a user without osteoarthritis pain. Reference line 82 contrasts the user's pain with an OA brace versus reference line 84 representing a user wearing the orthopedic device including both the OA brace and the controllable electrode. The overall pain is reduced compared to using an OA brace, and is much closer to that of the reference line 84 for a user without osteoarthritis.

At least one electrode and/or at least one sensor can be incorporated into the liner body itself or may alternatively be placed on the frames, struts or hinge of the brace support, or remotely from the brace support either on a garment or by themselves or by other known means. In another variation, at least one electrode and/or at least one sensor may be separately applied to the user's leg, both upper and/or lower leg portions, and/or at the knee by a garment or other type of attachment means. At least one electrode and/or at least one sensor may be placed into or onto sleeves, socks, bands, or as other layers of material that may be incorporated into the OA brace or other devices placed over the user's limbs.

At least one electrode and/or at least one sensor may be held in place through grooves, channels, pockets, and/or other attachment means. The pockets may have opened or closed ends for selectively installing or removing the at least one electrode and/or at least one sensor. Further, an array or electrodes and/or sensors may extend over the liner or other portions of the OA brace or separate components aimed to carry the at least one electrode and/or at least one sensor. The electrodes and/or sensors may be made of rigid, soft, or a combination of rigid and soft materials.

The control unit may be wirelessly connected or wired to the electrode or a plurality of electrodes at locations on the OA brace. The control unit may have a display and control keys permitting the user to select the various programs for activating the electrode. Various sensors or sensor modules may be located within the control box or placed at locations along the OA brace, as shown in FIG. 5 with sensors 76, 78 on the upper and lower frame elements 62, 64. These sensors may also be at the hinge 66, and/or the struts 72, 74.

A sensor module may include: kinematic sensors, single-axis gyroscopes, single- or multi-axis accelerometers, load sensors, flex sensors or myoelectric sensors. U.S. Pat. No. 5,955,667, granted Sep. 21, 1999, U.S. Pat. No. 6,301,964, granted Oct. 16, 2001, and U.S. Pat. No. 6,513,381, granted Feb. 4, 2003, also illustrate examples of sensors that may be used with embodiments of the disclosure, which patents are incorporated by reference in their entirety and be considered as part of this specification.

In certain embodiments, one or more acceleration sensors may include an XSENS acceleration sensor, such as the MT9 Inertial 3D motion tracker commercially available from XSENS Motion Technologies (Netherlands). In yet other embodiments, other suitable types of acceleration or movement reading sensors may also be used. The sensor module may include a gyroscope configured to measure angular speed. In other embodiments, the sensor module includes a plantar pressure sensor configured to measure the vertical plantar pressure of a specific underfoot area. Other movement signal(s) in a reference plane can also be utilized, such as measurements of centrifugal force, magnetic field and/or electromagnetic field.

A sensor module may be configured to detect gait patterns and/or events. The sensor module may determine whether the user is in a standing/stopped position, is walking on level ground, is ascending and/or descending stairs or sloped surfaces, or the like. The sensor module may detect when the user has moved to a relaxed position, such as sitting, crossing legs, reclining, lying down, crawling, leaning, etc. The sensor module may detect these relaxed positions by measuring combinations of vertical acceleration, horizontal/lateral acceleration, and time. In one embodiment, the measured vertical acceleration corresponds to the force of gravity.

In the embodiment of FIGS. 4 and 5, at least one sensor of the sensor module is incorporated or located with the electrode 70. Sensors may be placed at other locations, such as in the embodiment of FIG. 2.

The accelerometer may measure an angle of the lower limb relative to vertical, which may then determine an angle of the limb relative to the ground. As the limb rotates from the upright, vertical position, the corresponding force of gravity will vary relative to the degree of rotation. For instance, when the limb is in an upright, vertical position, the accelerometer may measure the standard force of gravity, 9.8 m/s2. As the limb rotates from the vertical position, the accelerometer may measure a fraction of the Earth's global force of gravity relative to the changing angle of the limb regarding the ground. A sensor module configured to measure acceleration in the vertical plane may determine the stationary angle of the limb regarding the ground.

In an example, the sensor module may indicate the limb is tilted at an angle of 90 deg. Regarding the ground. This might indicate, for example, that the user is lying completely flat on the back. Alternatively, the sensor module may indicate the limb is at an angle of 45 deg. Regarding the ground. That may indicate perhaps that the user is sitting down with legs outstretched in such a manner as to form a 45 deg. angle regarding the ground.

A ground contact sensor may be used in the orthopedic device wherein axial displacement of the sensor moving part represents the ground contact occurrence. In certain embodiments, the sensor moving part axial displacement is detected and/or measured with load cell, non-contact magnetic sensor, optical encoder, mechanical switch, magnetic switch; inductive sensor, capacitive sensor, magnetic encoder, reflective infrared sensor, piezoelectric sensor, Hall-effect sensor and conductive rubber.

While the exemplary embodiments describe the orthopedic device as used with an OA brace for treating osteoarthritis of the knee, a brace may be employed for treating other joints such as the elbow or shoulder.

The embodiments described may be adapted in prosthetic devices wherein a hard prosthetic socket and liner system may be equipped sensors and/or electrodes for stimulating function of the user's leg outside of the socket. Examples of sockets and liner systems are found in the following patents which are each incorporated in their entirety: U.S. Pat. No. 7,780,741, granted Aug. 24, 2010, U.S. Pat. No. 7,438,843, granted Oct. 21, 2008, and U.S. Pat. No. 5,718,925, granted Feb. 17, 1998. The extension of the orthopedic device embodiments is not limited to prosthetic sockets, but can be employed in other prosthetic components as well for rehabilitating residual limbs and intact limbs.

While the foregoing embodiments have been described and shown, alternatives and modifications of these embodiments, such as those suggested by others, may be made to fall within the scope of the disclosure. The principles described may be extended to other types of prosthetic or orthopedic devices.

The invention claimed is:

1. An orthopedic device comprising:
a brace support arranged for a knee and having at least one dynamic force strap for providing corrective orientation of a knee joint and unloading of the knee joint, the at least one dynamic force strap arranged to secure to upper and lower frame portions connected to one another by an upright including a hinge, a first end of the at least one dynamic force strap connected to the upper frame portion and a second end of the at least one dynamic force strap connected to the lower frame portion, the at least one dynamic force strap urging a force toward the upright during extension of the knee joint; and
an electrical stimulation system including a control unit, at least one electrode, and a sensor module, the sensor module arranged to detect movement and orientation of a user's leg, the control unit selectively operating the at least one electrode according to feedback from the sensor module, the feedback from the sensor module, the electrical stimulation system arranged to selectively generate, at certain stages of a user's gait, an electrical impulse by the at least one electrode delivered to a user's *vastus medialis* to provide stimulation to the *vastus medialis* depending on a load level going through an affected knee compartment in supplement to the corrective orientation of the knee joint resulting from the force applied by the at least one dynamic force strap.

2. The orthopedic device of claim 1, wherein the control unit is on a garment that holds the control unit as a user wears the device and undergoes movement, the control unit connects to the at least one electrode mounted on a thigh liner carried by an upper frame of the brace support.

3. The orthopedic device of claim 1, wherein the at least one electrode is located on a medial side of the brace support, and the at least one dynamic force strap including first and second dynamic force straps arranged to extend above and below, respectively, a knee joint on a lateral side of the brace support, the first and second dynamic force straps intersecting between the lateral and medial sides of the brace support.

4. The orthopedic device of claim 1, wherein the orthopedic device includes a garment disposed between the brace support and the user's leg, the garment arranged as a sleeve.

5. The orthopedic device of claim 4, wherein the upper frame portion is semi-rigid and the garment is substantially flexible and compressible, the at least one dynamic force strap is arranged to spiral between the upper frame portion and the lower frame portion.

6. The orthopedic device of claim 1, further comprising a garment located between the brace support and the user's leg, the garment carrying the at least one electrode.

* * * * *